United States Patent
Crook

(10) Patent No.: US 8,836,520 B1
(45) Date of Patent: Sep. 16, 2014

(54) HYDROGEN SULFIDE SENSOR WITH WATER DETECTION

(71) Applicant: Gary W. Crook, Midland, TX (US)

(72) Inventor: Gary W. Crook, Midland, TX (US)

( * ) Notice: Subject to any disclaimer, the term of this patent is extended or adjusted under 35 U.S.C. 154(b) by 58 days.

(21) Appl. No.: 13/777,248

(22) Filed: Feb. 26, 2013

Related U.S. Application Data

(60) Provisional application No. 61/605,563, filed on Mar. 1, 2012.

(51) Int. Cl.
*G08B 21/00* (2006.01)
*G08B 21/20* (2006.01)
*G01N 19/10* (2006.01)

(52) U.S. Cl.
CPC ............... *G08B 21/20* (2013.01); *G01N 19/10* (2013.01)
USPC ........... 340/604; 340/628; 340/630; 340/632; 340/631; 340/679

(58) Field of Classification Search
CPC ............................ G08B 21/20; G01S 13/003
USPC ................ 340/604, 628, 630, 632, 531, 679
See application file for complete search history.

(56) References Cited

U.S. PATENT DOCUMENTS

| | | | |
|---|---|---|---|
| 4,870,855 A | 10/1989 | Shafer | |
| 6,629,444 B2 * | 10/2003 | Peng | 73/1.06 |
| 6,675,826 B1 | 1/2004 | Newman et al. | |
| 6,856,253 B1 | 2/2005 | Crook | |
| 6,954,143 B2 | 10/2005 | Crook | |
| RE40,238 E | 4/2008 | Crook | |
| 7,463,160 B2 | 12/2008 | Crook | |
| 7,598,858 B2 | 10/2009 | Quist et al. | |
| 2006/0113199 A1 * | 6/2006 | Sasaki et al. | 205/783 |
| 2007/0159326 A1 * | 7/2007 | Quist et al. | 340/539.26 |
| 2010/0156647 A1 * | 6/2010 | Thorson | 340/632 |

* cited by examiner

*Primary Examiner* — Tai T Nguyen
(74) *Attorney, Agent, or Firm* — www.bobharter.com; Robert J. Harter

(57) ABSTRACT

An H2S (hydrogen sulfide) monitor includes a hydrogen sulfide sensor and a moisture sensor. In some examples, the H2S monitor emits a moisture alarm if the moisture sensor detects liquid water in an amount that exceeds or approaches a moisture tolerance limit of the hydrogen sulfide sensor. In some examples, the moisture sensor prevents the hydrogen sulfide sensor from triggering a false H2S alarm caused by moisture contaminating the hydrogen sulfide sensor.

16 Claims, 3 Drawing Sheets

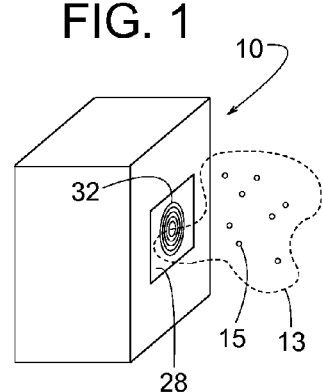
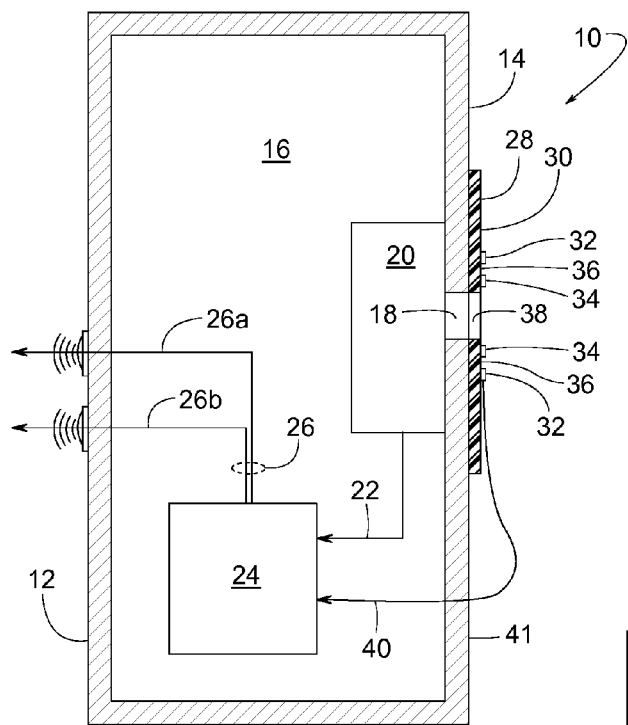
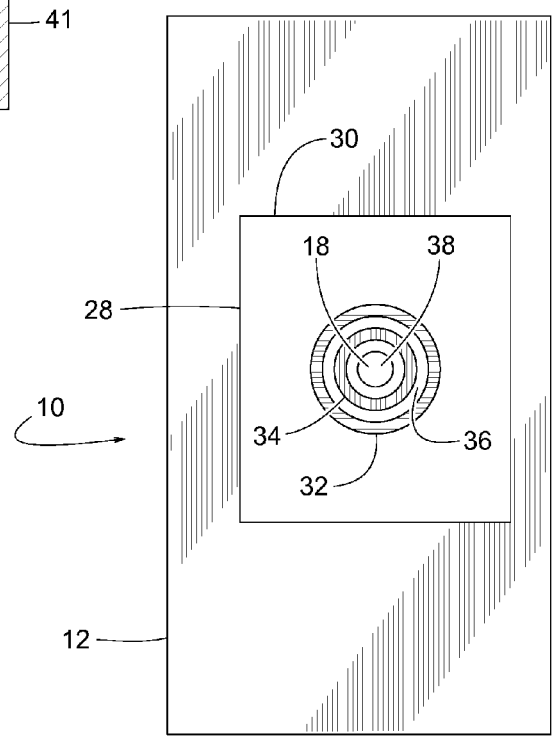

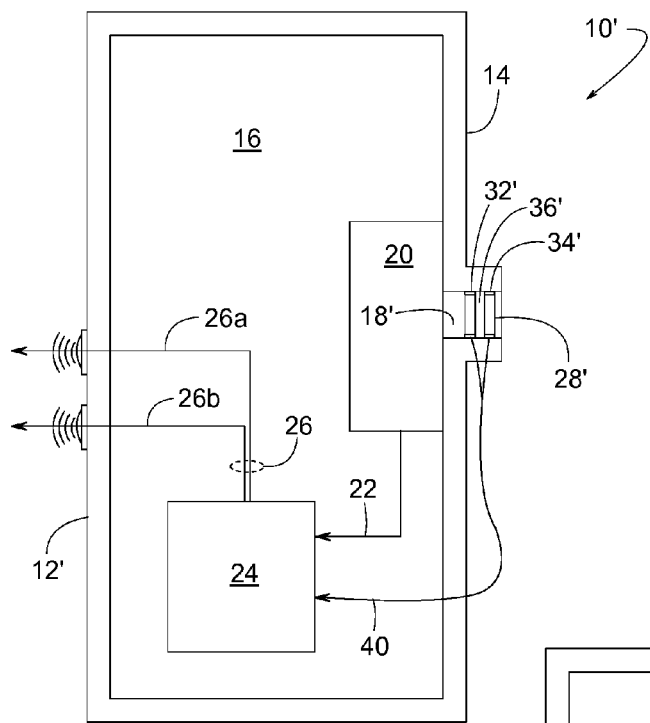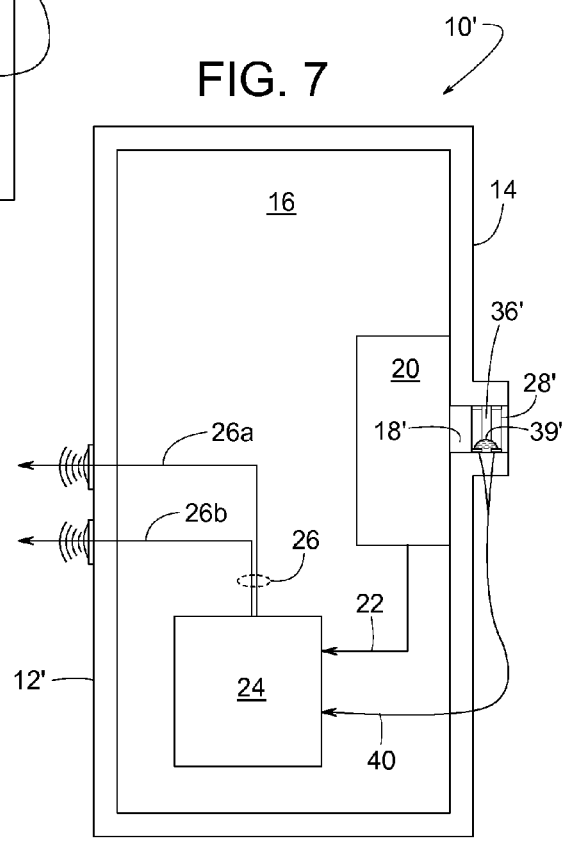

HYDROGEN SULFIDE SENSOR WITH WATER DETECTION

CROSS REFERENCE TO RELATED APPLICATIONS

This application claims the benefit of provisional patent application Ser. No. 61/605,563 filed on Mar. 1, 2012 by the present inventor.

FIELD OF THE DISCLOSURE

The subject invention generally pertains to monitoring of hydrogen sulfide gas of an environment and more specifically to means for recognizing a fault caused by an H2S monitor being contaminated with liquid water.

BACKGROUND

In some locations, it may be important to monitor the concentration of H2S (hydrogen sulfide) to alert people of hazardous levels of the gas. Various H2S monitors are available for that purpose. Examples of such monitors and related systems are disclosed in U.S. Pat. RE40,238; U.S. Pat. Nos. 6,954,143 and 7,463,160; all of which are specifically incorporated by reference herein.

BRIEF DESCRIPTION OF THE DRAWINGS

FIG. 1 is a perspective view of an example H2S monitor constructed in accordance with the teachings disclosed herein.

FIG. 2 is a cross-sectional schematic side view of the H2S monitor shown in FIG. 1.

FIG. 3 is a front view of FIG. 2.

FIG. 6 is a cross-sectional schematic side view similar to FIG. 2 but showing another example H2S monitor constructed in accordance with the teachings disclosed herein.

FIG. 7 is a cross-sectional schematic side view similar to FIG. 6 but showing a water droplet triggering the moisture sensor.

DETAILED DESCRIPTION

Figure 4:
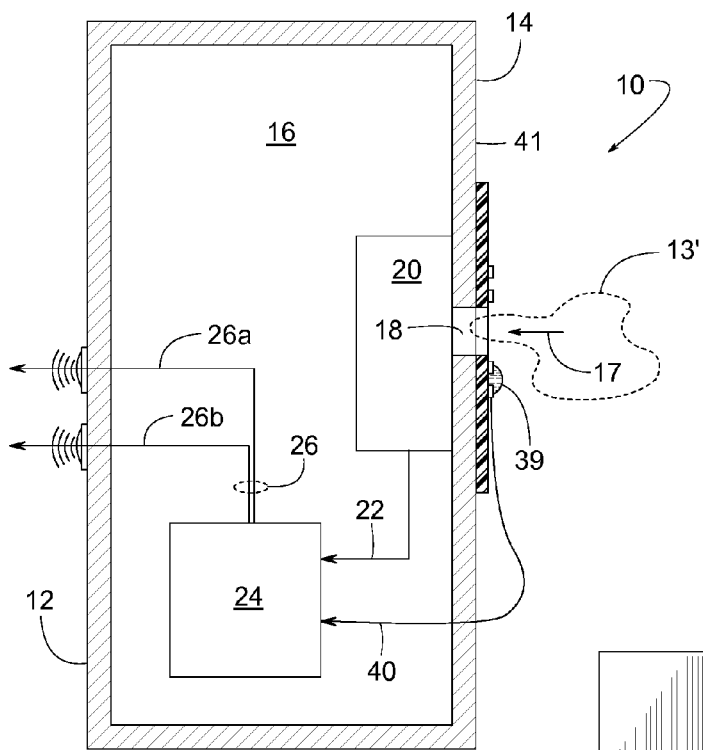
FIG. 4 is a cross-sectional schematic side view similar to FIG. 2 but showing a water droplet triggering the moisture sensor.
Figure 5:
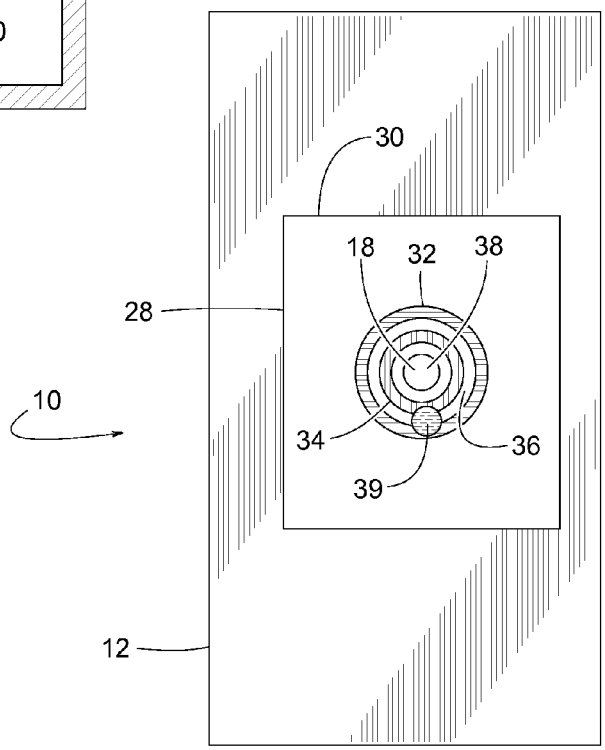
FIG. 5 is a front view of FIG. 4.

Referring to FIGS. 1-5, an example H2S monitor 10 is used for monitoring the concentration of hydrogen sulfide gas of an atmosphere 13 surrounding monitor 10, wherein atmosphere 13 might include a moisture component 15 (e.g., liquid water, droplets, rain, water spray, condensation, etc.). Upon detecting a predetermined concentration of hydrogen sulfide gas or a certain amount of liquid water, H2S monitor 10 responds accordingly by providing an appropriate alarm 26 (e.g., an H2S alarm 26a and/or a moisture alarm 26b).

In some examples, H2S monitor 10 comprises a housing 12 (e.g., an enclosure) defining an exterior 14, an interior 16, and an opening 18 through housing 12. A hydrogen sulfide sensor 20 (known by those of ordinary skill in the art) is disposed within the interior 16 of housing 12 in proximity with opening 18. In response to sensing hydrogen sulfide gas in a sample of gas 13' flowing, migrating or otherwise having traveled in a forward direction 17 toward H2S monitor 10, sensor 20 generates an H2S signal 22 (a first signal) that a controller 24 interprets for determining whether to output H2S alarm 26a (a first alarm such as a light, siren, text message, etc.). Controller 24 is schematically illustrated to represent any device (e.g., a microprocessor, computer, etc.) capable of providing outputs (e.g., alarm 26) in response to inputs (e.g., signal 22 or 40). Controller 24 commands H2S alarm 26a to be emitted if the atmosphere's concentration of hydrogen sulfide gas of sensed sample 13' exceeds a predetermined H2S concentration limit (e.g., 10 ppm).

In some examples, hydrogen sulfide sensor 20 has a predetermined moisture tolerance limit. Hydrogen sulfide sensor 20 has a sensing accuracy that is appreciably degraded when sensor 20 is exposed to liquid water of an amount that exceeds the sensor's predetermined moisture tolerance limit. The accuracy of hydrogen sulfide sensor 20 is a measure of how closely the hydrogen sulfide sensor's reading reflects the atmosphere's actual concentration of H2S gas.

To prevent hydrogen sulfide sensor 20 from triggering a false H2S alarm caused by moisture in the form of liquid water contaminating hydrogen sulfide sensor 20, H2S monitor 10 includes a moisture sensor 28 in proximity with opening 18 and/or in proximity with hydrogen sulfide sensor 20. In some examples, the term, "proximity" means that the locations are sufficiently close that the fluid conditions at the subject locations are comparable. In some examples, the proximity is such that moisture sensor 28 is within three inches of opening 18 and/or within three inches of hydrogen sulfide sensor 20. In some examples, moisture sensor 28 is on the exterior 14 of housing 12 and is upstream of hydrogen sulfide sensor 20, wherein the term, "upstream" is with respect to the approaching flow direction 17. In some examples, moisture sensor 28 is on the interior 16 of housing 12 but is still upstream of hydrogen sulfide sensor 20. In the example shown in FIGS. 6 and 7, a moisture sensor 28' is disposed within an opening 18' of a housing 12'.

In the example illustrated in FIGS. 1-5, moisture sensor 28 comprises a printed circuit board 30 (PCB 30) with two concentric uninsulated conductors 32 and 34 (water-sensing electrical contacts) that are radially separated by an insulated gap 36 (e.g., an air gap or bare portion of circuit board 30). To allow gas to reach hydrogen sulfide sensor 20, PCB 30 has a hole 38 aligned with hole 18 in housing 12. In the illustrated example, conductors 32 and 34 encircle hole 38 and face away from hydrogen sulfide sensor 20.

A liquid droplet of water 39, of a predetermined amount, from rain or other sources bridging gap 36 provides at least some electrical continuity between conductors 32 and 34, thereby generating a moisture signal 40 (e.g., a second signal such as an ohmic resistance value) indicative of moisture contamination exceeding a predetermined moisture alarm threshold. In some examples, the predetermined amount of liquid water is that which is sufficient to bridge gap 36. Thus, in some examples, atmosphere 13 even at 100 percent relative humidity is in itself less than the predetermined moisture alarm threshold.

In response to water 39 causing signal 40, controller 24 responds in various ways, examples of which include, but are not limited to, inhibiting alarm signal 26a from indicating there is a hydrogen sulfide problem, generating moisture alarm 26b (a second alarm such as a light, siren, text message, etc.) in such a way that alarm 26b indicates a moisture contamination fault, etc. In some examples, alarms 26a and 26b are distinguishable from each other by tone, number of pulses, frequency of pulses, pulse width or duration, amplitude, color, etc.

In the illustrated example where conductors 32 and 34 are on the exterior 14 of housing 12, an outer peripheral surface 41 of housing 12 is closer to the moisture sensor's conductors 32 and 34 than to hydrogen sulfide sensor 20. Outer peripheral surface 41 is the outermost envelope or 3D footprint of housing 12, thus opening 18 is not considered as being part of outer peripheral surface 41. In some examples, the expression, "the moisture sensor is on the exterior of the housing, and the hydrogen sulfide sensor is within the interior of the housing" means that at least part of the moisture sensor is on the exterior of the housing, and at least part of the hydrogen sulfide sensor is within the interior of the housing.

For greatest protection, in some examples, the predetermined moisture alarm threshold of moisture sensor 28 is less than the moisture tolerance limit of hydrogen sulfide sensor 20. To reduce the frequency of occurrence of H2S alarms 26b, in some examples, the predetermined moisture alarm threshold of moisture sensor 28 is greater than the moisture tolerance limit of hydrogen sulfide sensor 20. In some examples, the moisture tolerance limit, the predetermined moisture alarm threshold, and the moisture content of atmosphere 13 are quantified as a ratio of the mass of liquid water to the total mass of atmosphere in the local area of sampling.

In another example, shown in FIGS. 6 and 7, an H2S monitor 10' comprises a housing 12' with an opening 18' leading to hydrogen sulfide sensor 20. In this example, a moisture sensor 28' comprises two uninsulated annular conductors 32' and 34'. Conductors 32' and 34' are located in opening 18' and are axially separated by an insulated gap 36', whereby conductors 32' and 34' serve as water-sensing electrical contacts.

FIG. 6 shows moisture sensor 28' during normal dry conditions and operating below the moisture alarm threshold. FIG. 7 shows a liquid droplet of water 39' from rain or other sources bridging gap 36'. Water droplet 39' provides at least some electrical continuity between conductors 32' and 34', thereby generating a moisture signal 40 indicative of moisture contamination exceeding the predetermined moisture alarm threshold. In response to signal 40, controller 24 responds in various ways, examples of which include, but are not limited to, inhibiting alarm signal 26a from indicating there is a hydrogen sulfide problem, generating moisture alarm 26b in such a way that alarm 26b indicates a moisture contamination fault, etc.

In some examples, alarm signal 26 indicating a hydrogen sulfide problem or a moisture contamination problem is conveyed via wireless communication to a central station remote to H2S monitor 10. In some examples, housing 12 is at a generally fixed location at a worksite. In some examples, housing 12 is portable and carried or worn by a worker.

Other points worth noting include the following: Atmosphere is the fluid (gas and liquid) overlying or surrounding housing 12 in the area sensed by hydrogen sulfide sensor 20 and/or moisture sensor 28. The expression, "a sensor supported by the housing" means that at least some the sensor's weight is carried by or transmitted to the H2S monitor's housing. A hydrogen sulfide sensor is any device that provides an H2S signal in response to sensing hydrogen sulfide gas. The term, "hydrogen sulfide sensor" refers to the working elements of the sensor as opposed to a case or other parts that are not required for the sensor to provide an H2S signal in response to sensing hydrogen sulfide gas. A moisture sensor is any device that provides a moisture signal in response to sensing liquid water. The term, "moisture sensor" refers to the working elements of the sensor as opposed to a case or other parts that are not required for the sensor to provide a moisture signal in response to sensing liquid water. The terms, "H2S" and "hydrogen sulfide" are equivalent and used interchangeably herein. The expression, "the predetermined amount of liquid water has a water weight carried by the housing," is used as means for distinguishing liquid water droplets on a surface as opposed to humidity in the form of gaseous water carried by air.

Although the invention is described with respect to a preferred embodiment, modifications thereto will be apparent to those of ordinary skill in the art.

The scope of the invention, therefore, is to be determined by reference to the following claims:

1. An H2S monitor for monitoring an atmosphere, wherein the atmosphere includes a sample of gas flowing, migrating or otherwise traveling in an approaching flow direction toward the H2S monitor, the H2S monitor comprising:
    a housing defining an exterior, an interior and an opening through the housing;
    a hydrogen sulfide sensor disposed within the interior of the housing in proximity with the opening;
    a moisture sensor being supported by the housing in proximity with the opening, the moisture sensor, with respect to the approaching flow direction, being upstream of the hydrogen sulfide sensor, wherein the atmosphere contains moisture exposed to the moisture sensor;
    a predetermined moisture alarm threshold associated with the moisture sensor; and
    a moisture alarm emitted in response to the moisture sensor sensing that the moisture exceeds the predetermined moisture alarm threshold, the predetermined moisture alarm threshold being such that a predetermined amount of liquid water contacting the moisture sensor exceeds the predetermined moisture alarm threshold, and the atmosphere at 100 percent relative humidity is in itself less than the predetermined moisture alarm threshold.

2. The H2S monitor of claim 1, wherein the moisture sensor is on the exterior of the housing.

3. The H2S monitor of claim 1, wherein the moisture sensor includes two spaced-apart water-sensing electrical contacts on the exterior of the housing and facing away from the hydrogen sulfide sensor.

4. The H2S monitor of claim 1, wherein the moisture sensor has a predetermined moisture alarm threshold, and the H2S monitor further comprises a moisture alarm emitted in response to a predetermined amount of liquid water contacting the moisture sensor.

5. The H2S monitor of claim 1, wherein the moisture sensor has a predetermined moisture alarm threshold, and the H2S monitor further comprises a moisture alarm emitted in response to a predetermined amount of liquid water contacting the moisture sensor, wherein the predetermined amount of liquid water has a water weight carried by the housing.

6. The H2S monitor of claim 1, further comprising:
    a predetermined moisture tolerance limit associated with the hydrogen sulfide sensor, the hydrogen sulfide sensor having an accuracy that is appreciably degraded above the moisture tolerance limit;
    a predetermined H2S concentration limit associated with the hydrogen sulfide sensor;
    an H2S alarm emitted in response to the atmosphere having a concentration of H2S gas that exceeds the predetermined H2S concentration limit;
    a predetermined moisture alarm threshold associated with the moisture sensor, the predetermined moisture alarm threshold being less than the moisture tolerance limit of the hydrogen sulfide sensor; and
    a moisture alarm emitted in response to the moisture component, as sensed by the moisture sensor, being greater than the predetermined moisture alarm threshold.

7. An H2S monitor for monitoring an atmosphere, the H2S monitor comprising:

a housing having an outer peripheral surface facing the atmosphere, the housing defining an exterior, an interior and an opening through the housing;

a hydrogen sulfide sensor disposed within the interior of the housing in proximity with the opening such that the opening connects the hydrogen sulfide sensor in fluid communication with the atmosphere on the exterior of the housing;

a moisture sensor being supported by the housing in proximity with the opening, the outer peripheral surface being closer to the moisture sensor than to the hydrogen sulfide sensor a predetermined moisture tolerance limit associated with the hydrogen sulfide sensor, the hydrogen sulfide sensor having an accuracy that is appreciably degraded above the moisture tolerance limit;

a predetermined H2S concentration limit associated with the hydrogen sulfide sensor;

an H2S alarm emitted in response to the atmosphere having a concentration of H2S gas that exceeds the predetermined H2S concentration limit;

a predetermined moisture alarm threshold associated with the moisture sensor, the predetermined moisture alarm threshold being greater than the moisture tolerance limit of the hydrogen sulfide sensor; and a moisture alarm emitted in response to the moisture component, as sensed by the moisture sensor, being greater than the predetermined moisture alarm threshold.

8. The H2S monitor of claim 7, wherein the moisture sensor is on the exterior of the housing.

9. The H2S monitor of claim 7, wherein the moisture sensor includes two spaced-apart water-sensing electrical contacts on the exterior of the housing and facing away from the hydrogen sulfide sensor.

10. The H2S monitor of claim 7, wherein the moisture sensor has a predetermined moisture alarm threshold, and the H2S monitor further comprises a moisture alarm emitted in response to a predetermined amount of liquid water contacting the moisture sensor.

11. The H2S monitor of claim 7, wherein the moisture sensor has a predetermined moisture alarm threshold, and the H2S monitor further comprises a moisture alarm emitted in response to a predetermined amount of liquid water contacting the moisture sensor, wherein the predetermined amount of liquid water has a water weight carried by the housing.

12. The H2S monitor of claim 7, wherein the atmosphere contains moisture exposed to the moisture sensor, and the H2S monitor further comprising:

a predetermined moisture alarm threshold associated with the moisture sensor; and a moisture alarm emitted in response to the moisture sensor sensing that the moisture exceeds the predetermined moisture alarm threshold, the predetermined moisture alarm threshold being such that a predetermined amount of liquid water contacting the moisture sensor exceeds the predetermined moisture alarm threshold, and the atmosphere at 100 percent relative humidity is in itself less than the predetermined moisture alarm threshold.

13. An H2S monitor for monitoring an atmosphere, the H2S monitor comprising:

a housing defining an exterior and an interior, the exterior of the housing being exposed to the atmosphere;

an hydrogen sulfide sensor supported by the housing and being in fluid communication with the atmosphere, the hydrogen sulfide sensor having a moisture tolerance limit, the hydrogen sulfide sensor having an accuracy that is appreciably degraded above the moisture tolerance limit;

a predetermined H2S concentration limit associated with the hydrogen sulfide sensor;

an H2S alarm emitted in response to the atmosphere having a concentration of H2S gas that exceeds the predetermined H2S concentration limit;

a moisture sensor in proximity with the hydrogen sulfide sensor and being in fluid communication with the atmosphere;

a predetermined moisture alarm threshold associated with the moisture sensor; and a moisture alarm emitted in response to a predetermined amount of liquid water contacting the moisture sensor.

14. The H2S monitor of claim 13, wherein the moisture sensor is on the exterior of the housing, and the hydrogen sulfide sensor is within the interior of the housing.

15. The H2S monitor of claim 13, wherein the moisture sensor includes two spaced-apart water-sensing electrical contacts on the exterior of the housing and facing away from the hydrogen sulfide sensor.

16. The H2S monitor of claim 13, wherein the predetermined amount of liquid water contacting the moisture sensor has a water weight carried by the housing.

* * * * *